United States Patent
Spahn

(10) Patent No.: US 6,859,521 B2
(45) Date of Patent: Feb. 22, 2005

(54) METHOD AND ARRANGEMENT FOR CONTROLLING AN X-RAY BEAM

(75) Inventor: Martin Spahn, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 121 days.

(21) Appl. No.: 10/408,975

(22) Filed: Apr. 8, 2003

(65) Prior Publication Data

US 2003/0194056 A1 Oct. 16, 2003

(30) Foreign Application Priority Data

Apr. 16, 2002 (DE) .......................................... 102 16 857

(51) Int. Cl.$^7$ ................................................ H05G 1/58
(52) U.S. Cl. ........................ 378/117; 378/114; 378/115; 378/116; 378/197; 378/205
(58) Field of Search ..................... 378/91, 92, 114–117, 378/167, 189, 193, 196–198, 205–207; 600/407, 425, 429

(56) References Cited

U.S. PATENT DOCUMENTS

| | | | |
|---|---|---|---|
| 5,177,778 A | * | 1/1993 | Tsurumaki et al. ......... 378/117 |
| 5,572,566 A | | 11/1996 | Suzuki et al. ............... 378/98.2 |
| 6,200,024 B1 | | 3/2001 | Negrelli ....................... 378/197 |
| 6,302,580 B1 | * | 10/2001 | Dwyer, et al. .............. 378/197 |
| 6,435,715 B1 | * | 8/2002 | Betz et al. .................. 378/197 |
| 6,439,769 B1 | * | 8/2002 | Polkus et al. ............... 378/205 |
| 6,496,558 B2 | * | 12/2002 | Graumann .................... 378/39 |

FOREIGN PATENT DOCUMENTS

DE 30 24 294 1/1982

* cited by examiner

Primary Examiner—Allen C. Ho
(74) Attorney, Agent, or Firm—Schiff Hardin LLP

(57) ABSTRACT

In a method and apparatus for controlling an X-ray device having at least one X-ray tube and at least one X-ray detector, wherein the X-ray tube and/or the X-ray detector are movably arranged, before an activation of an X-ray tube indicated for a desired measurement, an automatic check is made out as to whether an X-ray detector indicated for the desired measurement is activated. Position data of the appertaining X-ray tube and/or appertaining X-ray detector are also automatically determined and using the identified position data, the relative positions of the appertaining X-ray tube and of the appertaining X-ray detector relative to one another are identified. The X-ray tube is enabled for activation, or is automatically activated, only when the X-ray detector is activated and the X-ray tube and the X-ray detector are suitably positioned relative to one another for the desired measurement.

21 Claims, 4 Drawing Sheets

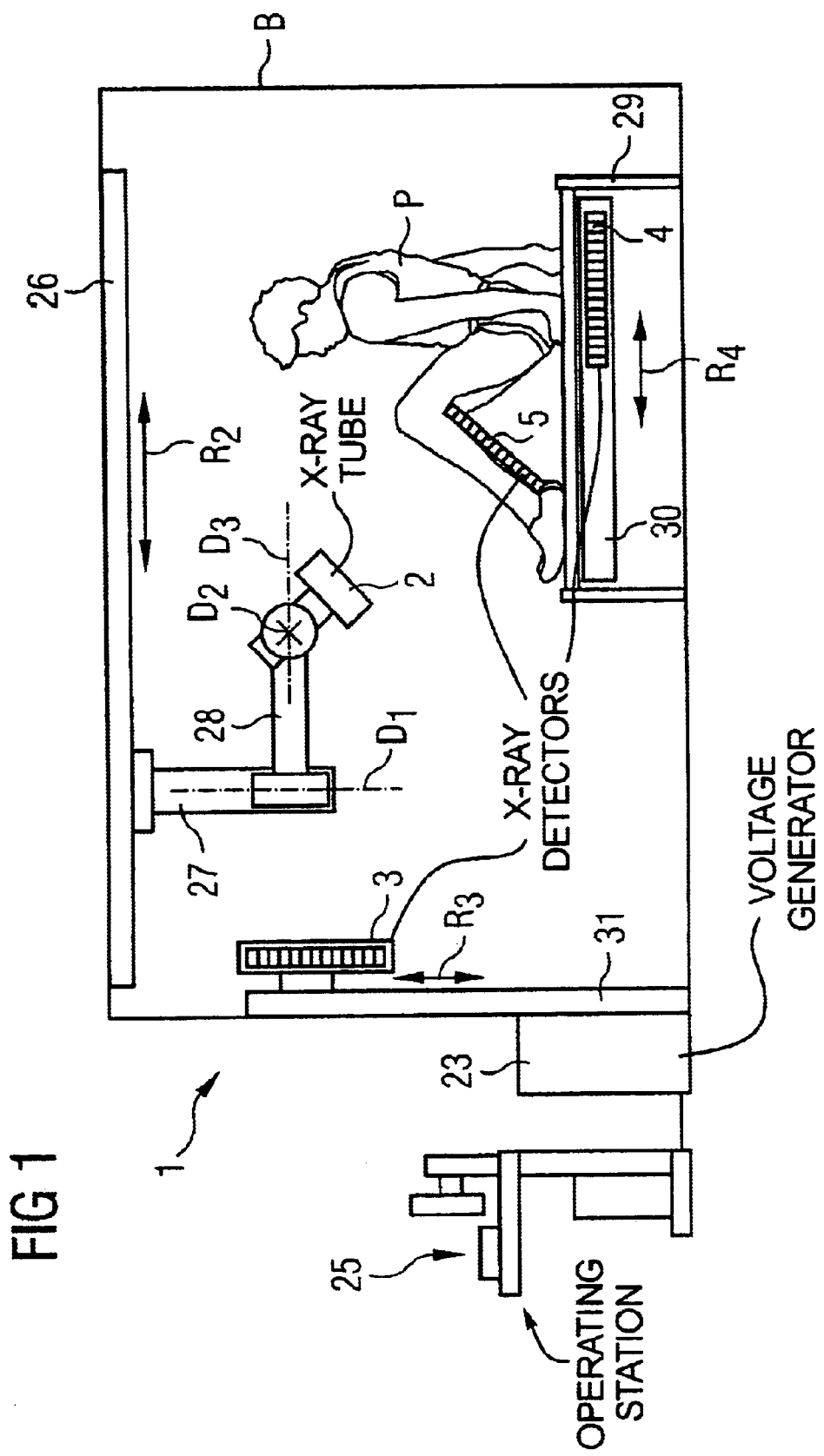

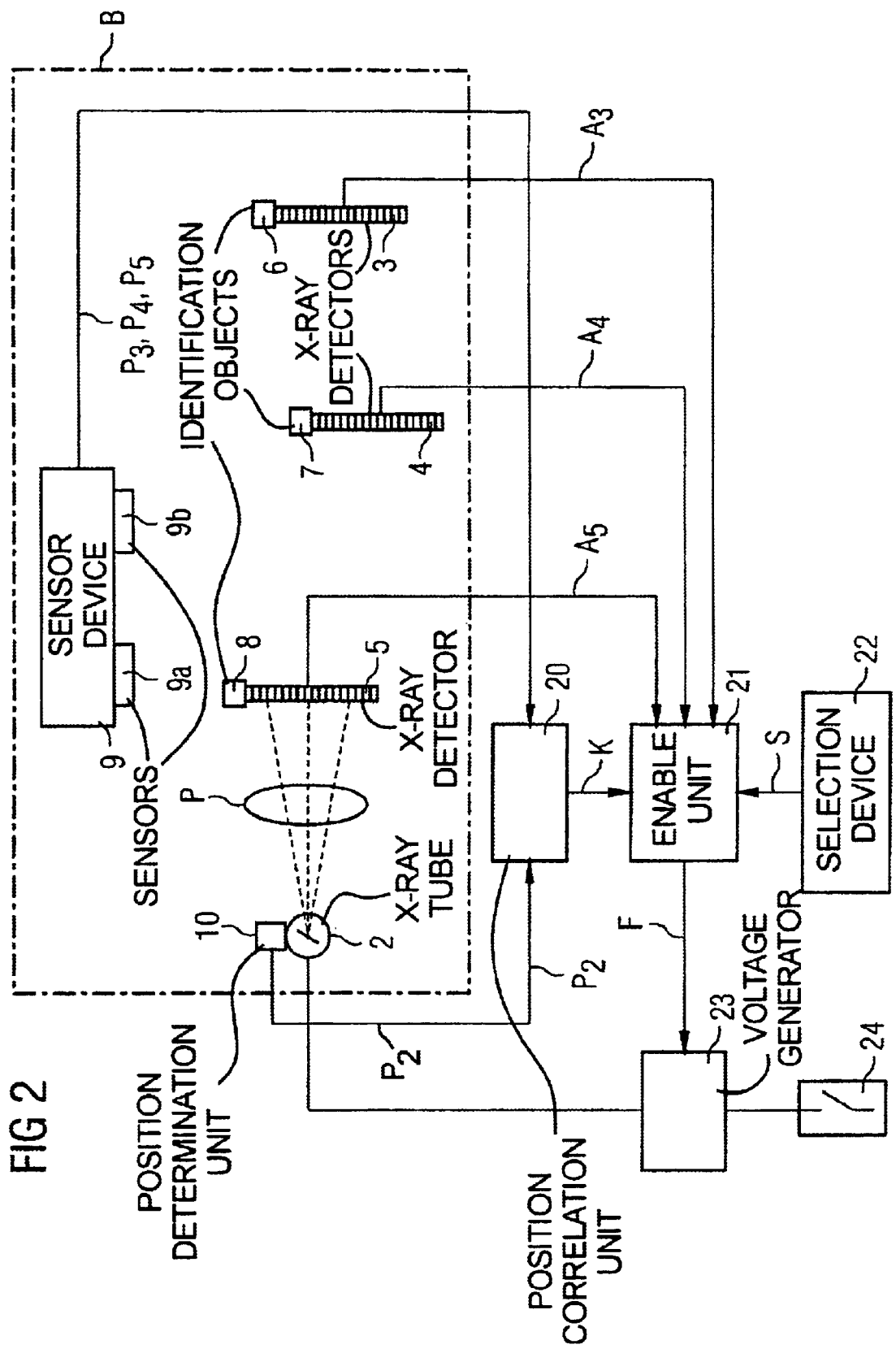

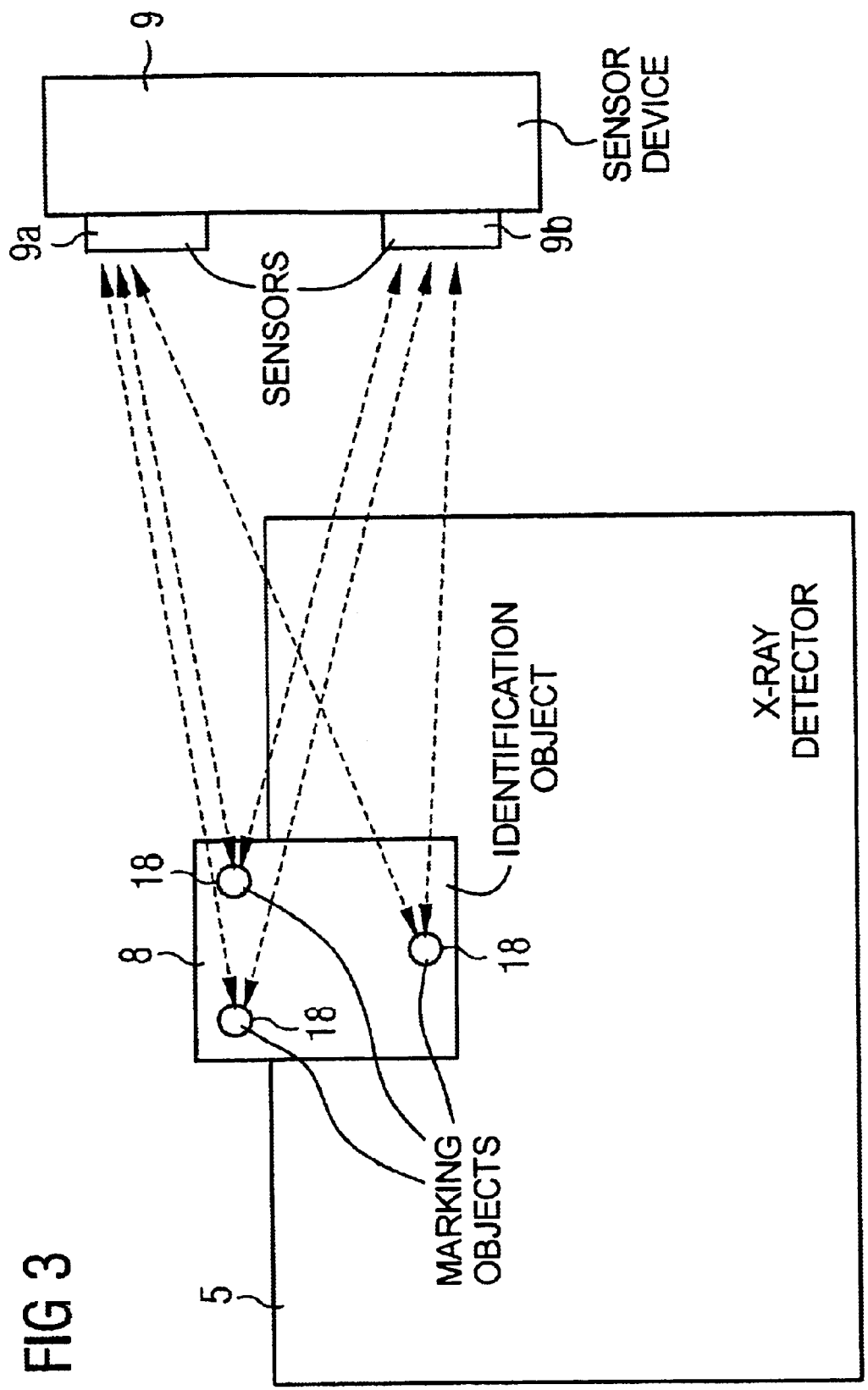

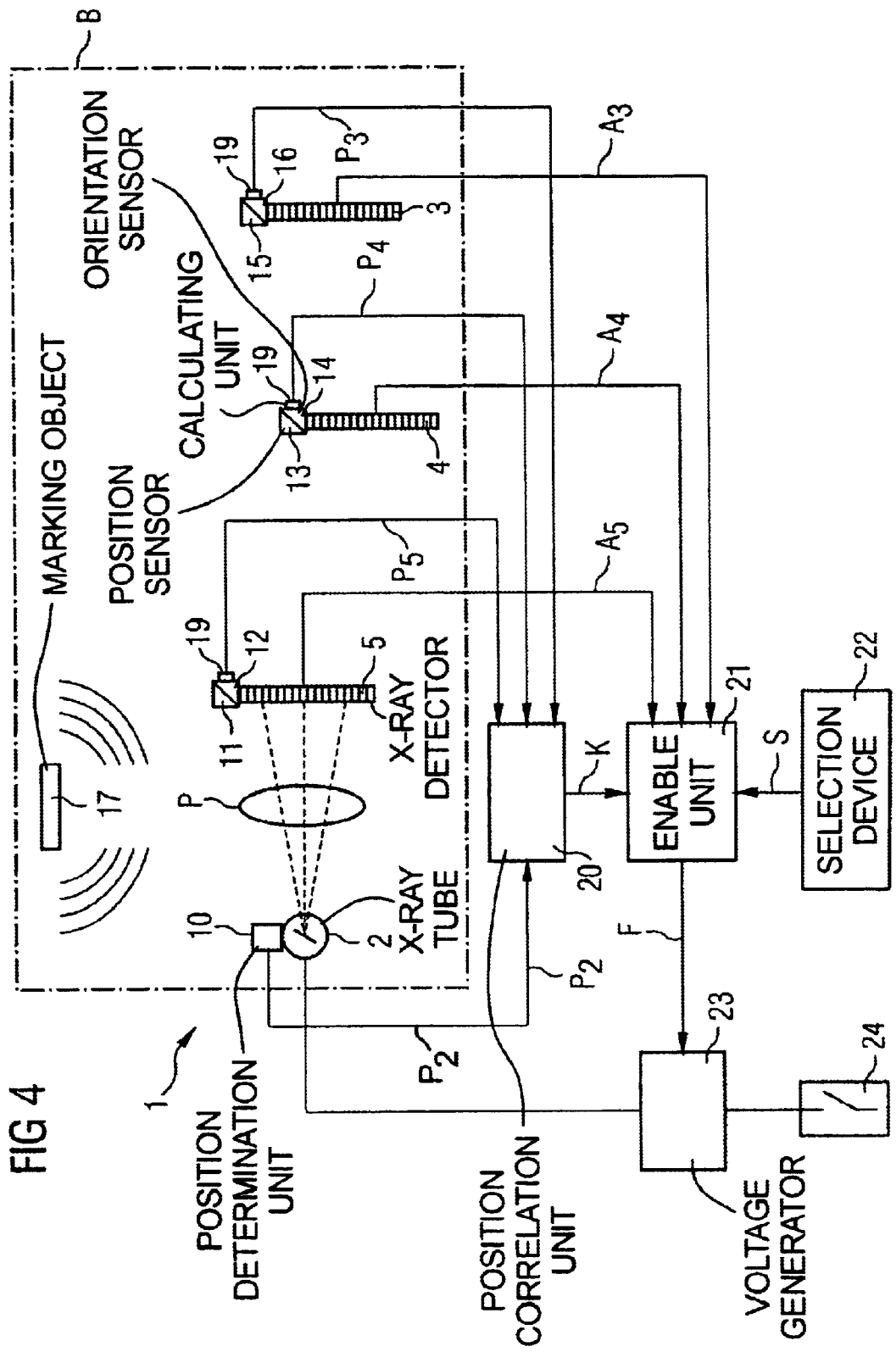

METHOD AND ARRANGEMENT FOR CONTROLLING AN X-RAY BEAM

BACKGROUND OF THE INVENTION

1. Field of the Invention

The present invention is directed to a method for controlling an X-ray device of the type having at least one X-ray tube and at least one X-ray detector, the X-ray tube and/or the X-ray detector being movably arranged. The invention also is directed to an X-ray device of this type.

2. Description of the Prior Art

Modern X-ray devices usually have not only a single X-ray tube/X-ray detector pair but generally contain a number of detectors that are permanently or movably installed or are mobile detectors. Either with or without a cable, such mobile detectors are freely movable at least within a range of action, for example within the X-ray room. A film foil cassette is an example of such a detector that is movable without a cable. The X-ray devices often additionally have a number of different fixed or movable X-ray tubes. An optimum system for implementing a specific examination is then constructed by selecting a detector and a matching X-ray tube. In the examination, it must then be assured that the desired X-ray tube and X-ray detector are suitably aligned relative to one another and relative to the examination subject, for example a body part of a patient, so that the X-rays passing through the examination subject strike the detector. It must also be assured that the corresponding detector is active and can pick up the X-rays. This is conventionally assured by an X-ray assistant, who aligns the X-ray tube and the X-ray detector relative to one another and relative to the examination subject and then determines that the corresponding detector is activated via a monitoring system attached to the X-ray detector, for example a flashing green light or a monitoring symbol displayed at an image station. The X-ray assistant then manually triggers the generation of the X-rays, and an image is acquired. When the X-rays are mistakenly triggered when the detector is not activated or when the X-ray tube and X-ray detector are not suitably positioned relative to one another, then the patient is exposed to the X-rays without the X-rays having an imaging effect. The exposure must then be repeated, which involves an additional radiation stress on the patient.

U.S. Pat. No. 6,200,024 discloses an X-ray diagnostic installation wherein the tube and the detector are respectively suspended independently of one another, compared to the known rigid connection of detector and tube via a C-arm, by means of which an active repositioning of the tube automatically effects an active repositioning of the detector or image intensifier. Mechanical sensors that know the respective location of the detector and the tube insure that a repositioning of the detector is automatically followed by a repositioning of the detector. The position of the detector and the tube thus can be acquired via the mechanical systems.

SUMMARY OF THE INVENTION

An object of the present invention is to minimize the existing safety risk of X-rays being triggered without the X-rays having an imaging effect at the correct detector.

This object is achieved in a method according to the invention wherein an automatic check is carried out before an activation of an X-ray tube indicated for a desired measurement, as to whether an X-ray detector indicated for the desired measurement is activated. Position data also are automatically determined, i.e. data about the position and/or orientation of the appertaining X-ray tube and/or appertaining X-ray detector. The term "position" as used herein covers both the location of an object as well as its orientation in space. Using the position data, the relative positions, i.e. the alignment and range, of the appertaining X-ray tube and of the appertaining X-ray detector relative to one another are identified. The X-ray tube is enabled for activation or is automatically activated only when the X-ray detector is activated and the X-ray tube and the X-ray detector are suitably positioned relative to one another for the desired measurement.

This object also is achieved in an inventive X-ray device of the type initially described having a position determination system for the automatic determination of position data of the movable X-ray tube indicated for the desired measurement and/or of the movable X-ray detector indicated for the desired measurement. A position correlation unit uses the position data to determine position correlation data that indicate the relative positions of the appertaining X-ray tube and of the appertaining X-ray detector with respect to one another. Further, an enable and/or trigger unit checks on the basis of the position correlation data as to whether the X-ray tube and the X-ray detector are correctly positioned relative to one another for the desired measurement. After determining that the current positioning of the X-ray tube and the X-ray detector exist as well as upon reception of an activation signal that indicates that the appertaining X-ray detector is activated this unit enables the X-ray tube for activation and/or automatically activates it.

The invention thus allows fully automated supervision of the alignment of the X-ray tube/X-ray detector pair by the X-ray assistant as well as the activation of the matching X-ray detector. An erroneous triggering of the X-rays are is thus prevented with high certainty.

A arbitrary number of X-ray tubes or X-ray detectors can be employed within the inventive X-ray device. The tubes and detectors can be installed so as to be fixed or movable, for example at a C-arm, within an examination table or at a wall mount. Preferably, however, at least one of the X-ray tubes and/or at least one of the X-ray detectors is freely movable at least within a field of use, for example the X-ray room, i.e. a mobile X-ray tube or X-ray detector is used. Such mobile devices allow an optimum matching to the location of the patient in the examination.

A large variety of position identification systems can be used for determining the positions of the X-ray tube and/or X-ray detector.

Insofar as one of the devices, for example the X-ray tube, is fixed, it suffices for the position data of this device to be determined once upon installation and stored in a memory so as to be fetchable therefrom for the inventive position monitoring. For devices that are movably installed at a carrier, for example a mount, a C-arm or in a table, the parameter values for the individual degrees of freedom of the movement of the respective device, for example an angular position of an articulation, can also be acquired and the exact position data of the respective device can be determined therefrom.

In a preferred embodiment, the X-ray device has a position determination system that operates in non-contacting fashion. Such a position determination system is particularly suitable for determining the position data of mobile X-ray tubes or X-ray detectors. A non-contacting measurement of the position data is possible, for example, with position determination systems that operate electromagnetically, for example by radio or optically, or that are based on ultrasound.

Stereotactic navigation methods can be used wherein a number of sensors observe an object in order to identify the exact position of the appertaining object. Such an object can be an active object such as, for example, a radio or infrared transmitter or can be a passive object that reflects radiation and/or, can simply be unambiguously optically identified with a CCD camera.

In a preferred embodiment, the position data of a number of marking objects respectively fixed at the X-ray tube or at the X-ray detector are determined relative to a sensor, by means of at least one sensor at a fixed position in the field of use, preferably be means of at least two sensors. The marking objects can be active or passive marking objects, for example reflective measuring points or the like that are matched to the respective sensors of the position determination system and that are additionally attached to the X-ray tube or, respectively, detector. Given utilization of a system that operates with conventional video cameras as sensors, specific, exactly identifiable parts of the X-ray tube or X-ray detector itself can be utilized as marking objects, for example specific edges of the housing. The position data of the appertaining X-ray tube or detector are then determined on the basis of the position data of the marking objects.

In another preferred embodiment, the direction and/or the range to a marking object positioned in a field of use are determined with at least one first sensor positioned at the respective X-ray tube or X-ray detector. The range measurement alternatively can ensue in such a way that the directions between the first sensor and two marking objects positioned in the field of use are determined and the range to the marking objects is determined by intersection. The orientation in space is then determined with a second sensor arranged at the respective X-ray tube or, respectively, detector. This second sensor can operate so that the orientation of the sensor itself, and thus the orientation of the X-ray tube or detector fixedly coupled with the sensor as well, is determined relative to the force of gravity. The desired position data of the respective X-ray tube or, respectively, detector then can be determined from the values for the range and the direction relative to one or more fixed points positioned in the field of use that are determined by the first sensor as well as from the data of the second sensor.

The large variety of position determination sub-systems can be combined to form a position determination system in accordance with the invention. For example, the position data of the X-ray tubes or detectors that are installed at movable carriers thus can be determined by means of a measurement of the setting parameters of the respective carrier, and the position data of freely movable X-ray tubes and/or detectors are determined by means of position determination systems that operate in non-contacting fashion. It is only important that all position data are known within a common, normalized coordinate system in order to be able to determine the relative positions of the individual devices with respect to one another.

In a preferred embodiment, the position determination system first determines the position data of all X-ray tubes or detectors belonging to the X-ray device and the relative positions of all device combinations relative to one another are determined therefrom. Subsequently, the relative positions for the X-ray tube/X-ray detector pair selected for the desired measurement are checked relative to one another on the basis of the available information about the correct position of the X-ray tube and of the X-ray detector relative to one another that is required for the examination.

This, for example, can occur so that the position determination system constantly automatically determines the position data of all X-ray tubes and detectors and forwards the data to the position correlation unit. The position correlation unit then determines the position correlation data of all X-ray tubes and detectors relative to one another and in turn forwards the data to the enable and/or trigger unit. The enable and/or trigger unit can be connected to a selection device that communicates selection data with which an X-ray tube/X-ray detector pair, selected for a desired measurement, is defined to the enable and/or trigger unit. The enable and/or trigger unit then reviews the position correlation data for the selected X-ray tube/X-rat detector pair on the basis of the selection data.

The selection device has a user interface for the entry of the selection data for selecting the X-ray tube/X-ray detector pair to be employed.

It is preferred for the selection device to contain an additional monitoring device that reviews whether an X-ray tube/X-ray detector pair that is correct for a desired application was selected. To this end, information about the desired examination or type of examination can also be entered into the selection device.

In a preferred embodiment, the suitable X-ray tube/X-ray detector pair is automatically selected on the basis of the information about the desired examination. For example, the X-ray assistant need merely enter a type of examination with a suitable user interface such as, for example, an X-ray exposure of the chest region of a standing patient. The selection device then automatically selects the suitable devices, for example a detector secured to a wall mount and an appertaining, suitably positioned X-ray tube.

After the correct positioning of the devices has been checked, the activity status of the desired X-ray detector is checked and, subsequently, enablement of the triggering of the appropriate X-ray tube is implemented, or the appertaining X-ray tube is automatically triggered.

DESCRIPTION OF THE DRAWINGS

FIG. 1 a schematically illustrates the arrangement of an X-ray tube as well as a number of X-ray detectors within an X-ray room.

FIG. 2 is a schematic illustration for explaining the determination of the position data of the X-tube and the X-ray detectors with a position determination system according to a first exemplary embodiment of the invention.

FIG. 3 is a more detailed illustration of an X-ray detector and the sensor from FIG. 2;

FIG. 4 is a schematic illustration for explaining the determination of the position data of the X-ray tube and the X-ray detectors with a position determination system according to a second exemplary embodiment of the invention.

DESCRIPTION OF THE PREFERRED EMBODIMENTS

The exemplary embodiment of an X-ray device 1 shown in FIG. 1 includes an X-ray tube 2 and three different X-ray detectors 3, 4, 5. The X-ray tube 2 and the X-ray detectors 3, 4, 5 are located within a field of use B, a standard, shielded X-ray room B in this case.

The X-ray tube 2 is secured to a ceiling mount that can be displaced along a motion direction R2 at a rail 26 secured to the ceiling of the X-ray room B. The ceiling mount is composed of a carrier rod 27 extending perpendicularly downwardly from the rail 26 and at which a swivel arm 28 is seated for pivoting around an axis D1 that proceeds coaxially with the carrier rod 27. The X-ray tube 2 is secured to the end of the swivel arm 28 so as to be pivotable around two further swiveling axes D2, D3 that proceed perpendicular to the first swiveling axis D1 and perpendicular to each other. The X-ray tube 2 is thus arranged in the X-ray room B so as to be movable in a total of four degrees of freedom, namely along the displacement direction R2 and along the three axes D1, D2, D3, and can thus be set into a large variety of positions in order to serve the respective X-ray detectors 3, 4, 5.

A first X-ray detector 3 is situated at a wall mount 31 and is adjustable in height along the motion direction R3. A second X-ray detector 4 is situated in a holder 30 under the bearing surface of an examination table 29 and is displaceable parallel to the table 29 along the motion direction R4. The X-ray device also has a completely freely movable, mobile X-ray detector 5.

FIG. 1 shows a situation wherein a patient P is seated on the examination table for X-raying the lower leg. The mobile detector 5 is used for this purpose. The mobile detector 5 is therefore positioned under the lower leg, and the patient P holds the leg in an angled attitude. The X-ray tube 2 is correspondingly configured such that it is suitably positioned relative to the X-ray detector 5, and the lower leg of the patient P is thereby situated in the correct position between the X-ray tube 2 and the X-ray detector 5.

A voltage generator 23 that is connected to the X-ray tube 2 and delivers the proper voltage for generating X-rays is situated outside the X-ray room B. An operating station 25 also is situated outside the X-ray room B, the voltage generator 23 being operated therefrom in order to trigger the X-rays. The individual X-ray detectors 3, 4, 5 also are connected to this operating station 25 via corresponding lines (not shown here). Insofar as digital X-ray detectors with an integrated readout unit are used, the image data can be sent directly via these lines to the operating station 25 and can be displayed thereat on a picture screen. Typical examples of such detectors are systems with optical coupling of an X-ray converter film to CCDs or CMOS chips, referred to as selenium-based detectors with electrostatic readout, or solid-state detectors with active readout matrices.

The mobile detector 5 can likewise be connected to the operating station 25 via a cable. Particularly the mobile detector 5 but also the other detectors 3, 5 as well, can also be connected to the operating station 25 via wireless interfaces, for example short-range radio interfaces, insofar as the respective detector 3, 4, 5 have an adequate energy supply, for example an accumulator.

The respective detectors 3, 4, 5 also can communicate their activity status to the operating device 25 via these lines or via wireless interfaces.

FIG. 2 shows an exemplary embodiment of how the positions of the X-ray tune and the individual X-ray detectors 3, 4, 5 are determined.

The X-ray tube 2 is equipped with a position determination device 10 that determines the position of the X-ray tube 2 on the basis of the settings of the angles in the rotational axes D1, D2, D3 of the ceiling mount 27, 28 as well as the position of the mount 27, 28 at the ceiling rail 26. The position determination device forwards the position data P2 to a position correlator 20 that, for example, is located within the operating station 25.

The positions of the detectors 3, 4, 5 are determined via a position system 6 through 9 that operate in non-contacting fashion, such as optically. To this end, a sensor device 9 having a number of individual sensors, two CCD cameras 9a, 9b in this case, is located at a suitable position inside the X-ray room B, for example at the ceiling.

Respective identification objects 6, 7, 8 are arranged fixed at the individual X-ray detectors 3, 4, 5, these objects 6, 7, 8 being unambiguously identified by the CCD cameras 9a, 9b and their position in the room being therefore able to be unambiguously defined by means of an observation with the CCD cameras 9a, 9b.

The functioning of this position determination method is explained in greater detail on the basis of FIG. 3 using the example of determining the position data P5 of the mobile detector 5. Here, the identification object 8 secured to the detector 5 has three marking objects 18 unambiguously positioned at the identification object 8. Due to the placement and/or the type of marking object 18, the respective identification object 8 or the detector 5 connected thereto can be unambiguously identified with the assistance of the CCD cameras 9a, 9b. The two CCD cameras 9a, 9b respectively acquire the identification object 8 with the three marking objects 18, and—from the two angles of view—can thus determine the location of every individual marking object 18, and thus the exact location as well as the orientation of the identification object 8.

The marking objects 18 can be active objects that they emit a signal, for example infrared radiation. However, they alternatively can be passive objects that, for example, reflect specific radiation to the sensors. The exemplary embodiment has CCD cameras that operate in the visible range. Simple hemispheres are employed here as the marking objects 18, these exhibiting a specific signal color so that they can be especially easily recognized and separated in the image signal of the CCD cameras 9a, 9b.

There are already various embodiments of such systems that use two sensors to acquire the position of a number of marking objects, and thus determine the location and the orientation of an object to be monitored. For example, the position determination system Polaris® of Northern Digital Inc. is such a commercially available system.

Alternatively, the marking objects 18 can be directly applied to the X-ray detector 5.

The position data P3, P4, P5 of the individual X-ray detectors 3, 4, 5 determined in this way by the sensor device 9 are likewise communicated to the position correlation unit 20.

In the position correlation unit 20, the position correlation data K that indicate the relative positions of the appertaining detector 3, 4, 5 relative to the X-ray tube 2 are then calculated from the position data P3, P4, P5 for all detectors 3, 4, 5 relative to the X-ray tube 2. These position correlation data K are then communicated to an enable unit 21. The enable unit 21 also receives respective activation signals A3, A4, A5 from the individual X-ray detectors 3, 4, 5, insofar as the appertaining X-ray detector 3, 4, 5 is activated.

The enable unit 21 is also connected to a selection device 22. This selection device 22 is a device with which the desired X-ray tube/X-ray detector pair 2, 5 is identified. The selection device 22 here is part of the operating station 25. For example, this can be a specific software module of control software of the X-ray device 1 installed on a computer of the operating station 25.

The selection device 22 communicates the selection data S that contain the information about the desired X-ray tube/X-ray detector pair 2, 5 to the enable unit 21. On the basis of the selection data S and the position correlation data K, the enables unit then reviews whether the selected X-ray tube and the X-ray detector in the X-ray tube/X-ray detector pair 2, 5 are suitably positioned relative to one another. When the review has proceeded successfully and when an activation signal A5 is also present for the appertaining X-ray detector 5, then an enable signal F is generated that is forwarded to the generator 23. This generator 23 then can be actuated with a switch 24 and the X-rays thus are triggered. The switch 24 alternatively can be part of the operating device 25. Moreover, the enable unit 21 and the position correlation unit 20 can alternatively be realized as software in a computer of the operating station 25.

Instead of the enable unit 21, a trigger unit can also be employed that automatically triggers the X-rays after receiving a suitable command and after a successful review of the positioning and of the detector activation.

FIG. 4 shows an alternative exemplary embodiment that largely agrees with the exemplary embodiment according to FIG. 2, so identical components are provided with the same reference characters in both Figures.

The significant difference between the X-ray device 1 according to FIG. 4 and the inventive X-ray device 1 according to FIG. 2 is in the position determination system.

In the exemplary embodiment according to FIG. 4, a position determination system is employed wherein a marking object 17 is positioned inside the X-ray room B. Respective sensors 15, 13, 11 are located at the X-ray detectors 3, 4, 5 for determining the range and the direction to the marking object 17. Dependent on the type of sensor 15, 13, 11, the marking object 17 can be an active marking object such as, for example, a radio or infrared transmitter, or can be a passive marking object.

The marking object 17 is a radio transmitter in the illustrated exemplary embodiment. The sensors 15, 13, 11 of the X-ray detectors 3, 4, 5 determine the direction from which the radio signal of the marking object (radio transmitter) 17 arrives and also recognize the distance from the marking object (radio transmitter) 17 on the basis of the received power. As a result the location of each sensor 15, 13, 11 in the room B is determined. Alternatively, a number of radio transmitters can be located in the room B, each emitting a radio signal that unambiguously identifies the transmitter. By means of a power measurement at each sensor 15, 13, 11 of the appertaining X-ray detectors, the range to each of the various transmitters can in turn be measured, and thus the position in the room B can also be determined by the range measurement.

The X-ray detectors 3, 4, 5 are also respectively equipped with orientation sensors 16, 14, 12 that serve for determining the orientation of the appertaining X-ray detector 3, 4, 5 in the room B. Various sensors with which the orientation in the room can be determined are well known.

Additionally, each of the X-ray detectors 3, 4, 5 has a calculating unit 19 that calculates the position data P3, P4, P5 from the identified range or direction to the marking object 17 positioned in the field of use, and from the orientation in the room B that was determined by the orientation respective sensor 16, 14, 12. The position data P3, P4, P5 are then forwarded to the position correlation unit 20. As in the exemplary embodiment according to FIG. 2, the position correlation unit 20 receives the position data P2 of the X-ray tube 2 directly from a measurement device 10 at the X-ray tube 2. The further processing of the position data P2, P3, P4, P5 and the linking with the activation signals A3, A4, A5 ensues as described in the exemplary embodiment according to FIG. 2.

The communication of the position data P3, P4, P5 of the individual X-ray detectors 3, 4, 5 to the position correlation unit 20 as well as the communication of the appertaining activation signals A3, A4, A5 to the enable unit 21 can ensure, dependent on the type of X-ray detector 3, 4, 5, to the position correlation unit 20 or to the enable unit 21 via a cable or by means a wireless transmission system, for example a radio interface.

Again it should be noted that the position determination systems shown in the figures are only exemplary embodiments of the invention, and a large variety of position determination methods can be used for determining the position of an arbitrary X-ray detector or X-ray tube. In the exemplary embodiment according to FIG. 4, for example, the position of the X-ray tube 2 can be determined in the same way via a non-contacting position determination system as in the case of the X-ray detectors 3, 4, 5. Different position determination systems likewise can be utilized for the various X-ray detectors 3, 4, 5.

Although further modifications and changes may be suggested by those skilled in the art, it is the intention of the inventors to embody within the patent warranted hereon all changes and modifications as reasonably and properly come within the scope of their contribution to the art.

I claim:

1. A method for controlling an X-ray device having at least one X-ray tube and at least one X-ray detector that is movable relative to said at least one X-ray tube, said method comprising the steps of:

before activating an X-ray tube, designated for an examination, to emit X-rays, automatically electronically checking whether an X-ray detector, also designated for said examination, has been activated;

automatically electronically obtaining position data identifying a position of at least one of said designated X-ray tube and said designated X-ray detector;

using said position data, automatically electronically determining respective positions of said designated X-ray tube and said designated X-ray detector relative to each other, and comparing said relative positions to correct relative positions for said examination; and allowing activation of said designated X-ray tube to emit X-rays in said examination only if said designated X-ray detector is activated and said designated X-ray tube and said designated X-ray detector are in said correct relative positions.

2. A method as claimed in claim 1 wherein the step of allowing activation of said designated X-ray tube comprises enabling manual activation of said designated X-ray tube.

3. A method as claimed in claim 1 wherein the step of allowing activation of said designated X-ray tube comprises automatically electronically triggering said designated X-ray tube.

4. A method as claimed in claim 1 wherein said at least one X-ray tube is freely movable within a field of use for conducting different types of examinations.

5. A method as claimed in claim 1 wherein said at least one X-ray detector is freely movable within a field of use for conducting different types of examinations.

6. A method as claimed in claim 1 wherein the step of automatically electronically obtaining position data comprises automatically electronically obtaining position data identifying a position of at least one of said designated X-ray tube and said designated X-ray detector using a non-contacting position determination system.

7. A method as claimed in claim 6 comprising employing an optical position detection system as said position determination system.

8. A method as claimed in claim 1 wherein said X-ray device comprises a plurality of X-ray tubes and a plurality of X-ray detectors, and wherein the step of automatically electronically obtaining position data comprises automatically electronically obtaining position data identifying respective positions of all of said X-ray tubes and respective positions of all of said X-ray detectors, and wherein the step of determining the relative position comprises determining, from said position data, relative positions of all of said X-ray tubes and all of said X-ray detectors relative to each other, and identifying the relative position, from among said relative positions, of said designated X-ray tube and said designated X-ray detector for comparison to said correct relative position.

9. A method as claimed in claim 1 wherein the step of automatically electronically obtaining position data for all of said X-ray tubes and all of said X-ray detector comprises affixing marking objects to each of said X-ray tubes and each of said X-ray detectors so that each of said X-ray tubes has a plurality of said marking objects affixed thereto, and each of said X-ray detectors has a plurality of said marking objects affixed thereto, detecting each plurality of marking objects with a sensor and determining position data for each plurality of marking objects, and determining said position data for the respective X-ray tubes and the respective X-ray detectors from the position data for each plurality of marking objects.

10. A method as claimed in claim 1 wherein the step of automatically electronically obtaining position data comprises affixing a sensor to each of said X-ray tubes and each of said X-ray detectors, disposing a marking object in a field of use of said X-ray tubes and X-ray detectors, identifying at least one of a direction and range of each sensor relative to said marking object, and determining said position data for the respective X-ray tubes and the respective X-ray detectors from said at least one of said detection and range for each sensor.

11. An X-ray system comprising:

at least one X-ray tube;

at least one X-ray detector that is movable relative to said at least one X-ray tube;

a position determination system for automatically electronically obtaining position data identifying a position of at least one of an X-ray tube designated for an examination and an X-ray detector designated for said examination, before activating said designated X-ray tube to emit X-rays in said examination;

a position correlation unit for, using said position data, automatically electronically determining respective positions of said designated X-ray tube and said designated X-ray detector relative to each other, and for comparing said relative positions to correct relative positions for said examination; and an activation unit which checks whether said designated X-ray detector is activated and which allows activation of said designated X-ray tube to emit X-rays in said examination only if said designated X-ray detector is activated and said designated X-ray tube and said designated X-ray detector are in said correct relative positions.

12. An X-ray system as claimed in claim 11 wherein said activation unit enables manual activation of said designated X-ray tube.

13. An X-ray system as claimed in claim 11 said activation unit automatically electronically triggers said designated X-ray tube.

14. An X-ray system as claimed in claim 11 wherein said at least one X-ray tube is freely movable within a field of use for conducting different types of examinations.

15. An X-ray system as claimed in claim 11 wherein said at least one X-ray detector is freely movable within a field of use for conducting different types of examinations.

16. An X-ray system as claimed in claim 11 wherein said position determination system is a non-contacting position determination system.

17. An X-ray system as claimed in claim 16 wherein said position determination system is an optical position detection system.

18. An X-ray system as claimed in claim 11 comprising a plurality of X-ray tubes and a plurality of X-ray detectors, and wherein said position determination system automatically electronically obtains position data identifying respective positions of all of said X-ray tubes and respective positions of all of said X-ray detectors, and wherein said position correlation unit determines, from said position data, relative positions of all of said X-ray tubes and all of said X-ray detectors relative to each other, and identifies the relative position, from among said relative positions, of said designated X-ray tube and said designated X-ray detector for comparison to said correct relative position.

19. An X-ray system as claimed in claim 11 wherein said position determination system comprises marking objects affixed to each of said X-ray tubes and each of said X-ray detectors so that each of said X-ray tubes has a plurality of said marking objects affixed thereto, and each of said X-ray detectors has a plurality of said marking objects affixed thereto, a sensor for detecting each plurality of marking objects and determining position data for each plurality of marking objects, and a unit for determining said position data for the respective X-ray tubes and the respective X-ray detectors from the position data for each plurality of marking objects.

20. An X-ray system as claimed in claim 11 wherein said position determination system comprises respective sensors affixed to said X-ray tubes and to said X-ray detectors, a marking object disposed in a field of use of said X-ray tubes and X-ray detectors, and a unit for identifying at least one of a direction and range of each sensor relative to said marking object, and for determining said position data for the respective X-ray tubes and the respective X-ray detectors from said at least one of said detection and range for each sensor.

21. An X-ray system as claimed in claim 11 comprising a selection unit for receiving an input designating an X-ray tube as said designated X-ray tube and designating an X-ray detector as said designated X-ray detector.

* * * * *